US012613265B2

(12) United States Patent
Song et al.

(10) Patent No.: US 12,613,265 B2
(45) Date of Patent: Apr. 28, 2026

(54) APPARATUS AND METHOD OF FOCUSING RADIO WAVE ENERGY

(71) Applicant: ELECTRONICS AND TELECOMMUNICATIONS RESEARCH INSTITUTE, Daejeon (KR)

(72) Inventors: Won Young Song, Daejeon (KR); Kwang Jae Lee, Daejeon (KR); Soon Ik Jeon, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 850 days.

(21) Appl. No.: 17/978,127

(22) Filed: Oct. 31, 2022

(65) Prior Publication Data

US 2023/0324446 A1     Oct. 12, 2023

(30) Foreign Application Priority Data

Mar. 25, 2022    (KR) ........................ 10-2022-0037353

(51) Int. Cl.
| | |
|---|---|
| *G01R 29/00* | (2006.01) |
| *A61N 5/00* | (2006.01) |
| *A61N 5/10* | (2006.01) |
| *G01R 29/10* | (2006.01) |

(52) U.S. Cl.
CPC ........... *G01R 29/10* (2013.01); *A61N 5/1031* (2013.01)

(58) Field of Classification Search
CPC .............................. G01R 29/10; A61N 5/1031
USPC ............................................................. 703/5
See application file for complete search history.

(56) References Cited

U.S. PATENT DOCUMENTS

| | | |
|---|---|---|
| 10,994,144 B1 | 5/2021 | John |
| 2009/0088625 A1 | 4/2009 | Oosting et al. |
| 2018/0250522 A1 | 9/2018 | Jeon et al. |
| 2018/0264281 A1 | 9/2018 | Kim et al. |
| 2021/0252314 A1 | 8/2021 | Sverdlik et al. |

(Continued)

FOREIGN PATENT DOCUMENTS

| | | |
|---|---|---|
| KR | 20180106453 A | 10/2018 |
| KR | 20210129852 A | 10/2021 |
| KR | 20220016566 A | 2/2022 |

(Continued)

OTHER PUBLICATIONS

Yongxing Li and Richard Smith, "Forward modeling of radio imaging (RIM) data with the Comsol RF module," Sep. 3, 2025, Computers and Geosciences, Science Direct, Elsevier, p. 60-67. (Year: 2015).*

*Primary Examiner* — Tiffany P Young
(74) *Attorney, Agent, or Firm* — Rabin & Berdo, P.C.

(57)     ABSTRACT

A method of focusing radio wave energy at a focusing target point, which is performed by a processor, may comprise: generating an electromagnetic numerical model of an object including the focusing target point; predicting radio wave focusing points inside the object using radio wave characteristic information of a radio wave radiation module and the electromagnetic numerical model; optimizing one or more focusing parameters such that radio wave energy reaching one or more unnecessary focusing points other than the focusing target point among the radio wave focusing points inside the object is reduced; and radiating radio waves based on the optimized focusing parameters.

20 Claims, 8 Drawing Sheets

(56) References Cited

U.S. PATENT DOCUMENTS

2021/0370103 A1    12/2021  Agarwal et al.

FOREIGN PATENT DOCUMENTS

| WO | 2020112688 A1 | 6/2020 |
| WO | 2020206146 A1 | 10/2020 |

* cited by examiner

FIG. 5A

APPARATUS AND METHOD OF FOCUSING RADIO WAVE ENERGY

CROSS-REFERENCE TO RELATED APPLICATIONS

This application claims priority to Korean Patent Application No. 10-2022-0037353 filed on Mar. 25, 2022 with the Korean Intellectual Property Office (KIPO), the entire contents of which are hereby incorporated by reference.

BACKGROUND

1. Technical Field

Example embodiments of the present disclosure relate to technology for focusing radio wave energy, and more particularly, to an apparatus and method for focusing radio wave energy, in which, when radio wave energy is focused, an unnecessary focusing point is removed to focus the radio wave energy only at a desired focusing point.

2. Related Art

The information disclosed in this section is only to provide background information about the present example embodiments and does not form the related art.

Among age-related diseases in an aging society, refractory diseases such as cancer, degenerative musculoskeletal diseases, and the like are generally treated through invasive treatment methods such as incisional surgery. Since such invasive treatment methods are based on surgical treatment, there is a risk of side effects such as pain, physical burden, and sequelae in all general patients as well as elderly patients.

In order to remedy such disadvantages of invasive treatment methods, non-invasive treatment technology for radiating high-density energy from the outside of a living body to treat a lesion inside the living body is gaining attention.

Such non-invasive treatment methods include radiation/ultrasound treatment, but due to a problem of radiation exposure and a problem of ultrasound being restricted by structures such as bones or by air, a safer non-invasive treatment method using radio wave energy that is not restricted by structures is being researched.

Since non-invasive radio wave energy treatment is technology for treating a lesion by radiating radio waves from the outside of a living body and applying heat to the lesion, the key is to correctly transmit radio wave energy to a target lesion. However, when a large amount of radio wave energy is also transmitted to an undesired area other than the lesion during the transmission of radio wave energy, a problem of adversely affecting a normal area occurs.

In order to solve the above problems, in an existing method, a temperature monitoring device and a cooling device for cooling are required, or a medical professional monitors a system at all times during treatment and stops the system when a problem occurs and performs work of re-operating the system after a certain period of time.

SUMMARY

Accordingly, example embodiments of the present disclosure are provided to substantially obviate one or more problems due to limitations and disadvantages of the related art.

Example embodiments of the present disclosure provide a method and apparatus for focusing radio wave energy in which an unnecessary focusing point is removed such that radio waves are not focused at a point other than a focusing target point.

Example embodiments of the present disclosure also provide a method of optimizing a focusing parameter in which a process of removing an unnecessary focusing point is repeatedly performed such that radio waves are not focused at a point other than a focusing target point.

According to a first exemplary embodiment of the present disclosure, a method of focusing radio wave energy at a focusing target point, which is performed by a processor, may comprise: generating an electromagnetic numerical model of an object including the focusing target point; predicting radio wave focusing points inside the object using radio wave characteristic information of a radio wave radiation module and the electromagnetic numerical model; optimizing one or more focusing parameters such that radio wave energy reaching one or more unnecessary focusing points other than the focusing target point among the radio wave focusing points inside the object is reduced; and radiating radio waves based on the optimized focusing parameters.

The electromagnetic numerical model may be generated using an internal tomography image of the object.

The generating of the electromagnetic numerical model may further include a preliminary measurement operation of acquiring information about permittivity, conductivity, and/or impedance of the object using the radio waves to be radiated; and the electromagnetic numerical model may be generated based on a result of the preliminary measurement operation.

A magnitude and a phase of the radio waves may be adjusted using the optimized focusing parameters.

The optimizing of the focusing parameters may include: operation (a) of extracting the unnecessary focusing points inside the object based on a first focusing parameter; operation (b) of calculating a second focusing parameter for reducing the radio wave energy focused on the extracted unnecessary focusing points; operation (c) of predicting the radio wave focusing points inside the object based on the second focusing parameter; and an operation of repeatedly performing operations (a) to (c) before the unnecessary focusing points are not extracted.

The unnecessary focusing points may be points having an intermediate value among points in the object at which the radio wave energy is focused to exceed a certain threshold value.

The calculating of the second focusing parameter may further include: calculating a parameter having a reverse phase of the radio wave energy focused at the unnecessary focusing points; and combining the first focusing parameter and the parameter having the reverse phase.

The parameter having the reverse phase at the unnecessary focusing points may be orthogonal to an electromagnetic characteristic value at the focusing target point.

According to a second exemplary embodiment of the present disclosure, an apparatus for focusing radio wave energy may comprise: a memory in which one or more instructions are stored; and a processor configured to execute the one or more instructions stored in the memory, wherein the processor configured to execute the one or more instructions performs: an operation of generating an electromagnetic numerical model of an object including a focusing target point; an operation of predicting radio wave focusing points inside the object using radio wave characteristic information of a radio wave radiation module and the electromagnetic numerical model: an operation of optimizing one or more focusing parameters such that radio wave energy reaching one or more unnecessary focusing points other than the focusing target point among the radio wave focusing points inside the object is reduced; and an operation of radiating radio waves based on the optimized focusing parameters.

The electromagnetic numerical model may be generated using an internal tomography image of the object.

The operation of, by the processor, generating the electromagnetic numerical model further may include a preliminary measurement operation of acquiring information about permittivity, conductivity, and/or impedance of the object using the radio waves to be radiated; and the electromagnetic numerical model may be generated based on a result of the preliminary measurement operation.

A magnitude and a phase of the radio waves may be adjusted using the optimized focusing parameters.

The operation of, by the processor, optimizing the focusing parameters may include: operation (a) of extracting the unnecessary focusing points inside the object based on a first focusing parameter; operation (b) of calculating a second focusing parameter for reducing the radio wave energy focused on the extracted unnecessary focusing points; operation (c) of predicting the radio wave focusing points inside the object based on the second focusing parameter; and an operation of repeatedly performing operations (a) to (c) before the unnecessary focusing points are not be extracted.

The unnecessary focusing points may be points having an intermediate value among points in the object at which the radio wave energy is focused to exceed a certain threshold value.

The operation of, by the processor, calculating the second focusing parameter may further include: calculating a parameter having a reverse phase of the radio wave energy focused at the unnecessary focusing points; and combining the first focusing parameter and the parameter having the reverse phase.

The parameter having the reverse phase at the unnecessary focusing points may be orthogonal to an electromagnetic characteristic value at the focusing target point.

According to a third exemplary embodiment of the present disclosure, a method of optimizing one or more focusing parameters, which is executed by a processor, may comprise: operation (a) of extracting one or more unnecessary focusing points inside an object including a focusing target point based on a first focusing parameter; operation (b) of calculating a second focusing parameter for reducing radio wave energy focused on the extracted unnecessary focusing points; operation (c) of predicting one or more radio wave focusing points inside the object based on the second focusing parameter; an operation of repeatedly performing operations (a) to (c) before the unnecessary focusing points may not be extracted; and an operation of outputting the second focusing parameter in which the unnecessary focusing points are not extracted.

The unnecessary focusing points may be points having an intermediate value among points in the object at which the radio wave energy is focused to exceed a certain threshold value.

The operation of, by the processor, calculating the second focusing parameter may further include: calculating a parameter having a reverse phase of the radio wave energy focused at the unnecessary focusing points; and combining the first focusing parameter and the parameter having the reverse phase.

The parameter having the reverse phase at the unnecessary focusing points may be orthogonal to an electromagnetic characteristic value at the focusing target point.

According to the present disclosure, in a method and apparatus for focusing radio wave energy, which removes an unnecessary focusing point, when high-density radio wave energy is transmitted to a focusing target point, it is possible to prevent radio waves from being focused in an unwanted area and efficiently focus the radio wave energy at the focusing target point. In particular, it is possible to solve problems in which, in an existing method and apparatus for focusing radio wave energy, since energy may be focused in an undesired area, an additional heat detecting device and cooling device are required or a monitoring process by medical personnel is required, and it is possible to enable high-efficiency radio wave energy to be focused at a target point without increasing system complexity.

In addition, the present disclosure is technology for radiating radio waves by calculating a focusing parameter in which radio waves are focused at points other than a target point through a process of optimizing a focusing parameter and thus is applicable not only to heat treatment using radio waves but also to various radio wave energy transmitting apparatuses.

In particular, according to the present disclosure, radio waves are prevented from being focused anywhere other than a desired position to prevent the occurrence of a problem in which, during non-invasive radio wave energy heat treatment on a living body, heat is applied to a normal area other than a lesion and adversely affects the normal area. Thus, it is possible to construct a system for focusing radio waves, which prevents a rise of a temperature of an undesired area without causing system complexity, thereby obtaining an effect in which safe heat treatment is possible without a problem in which a normal area other than a lesion area is destroyed by heat.

BRIEF DESCRIPTION OF DRAWINGS

FIGS. 5A to 5D show diagrams showing results of using an apparatus for removing the unnecessary focusing point 30 according to one example embodiment of the present disclosure.

DETAILED DESCRIPTION OF THE EMBODIMENTS

Figure 1:
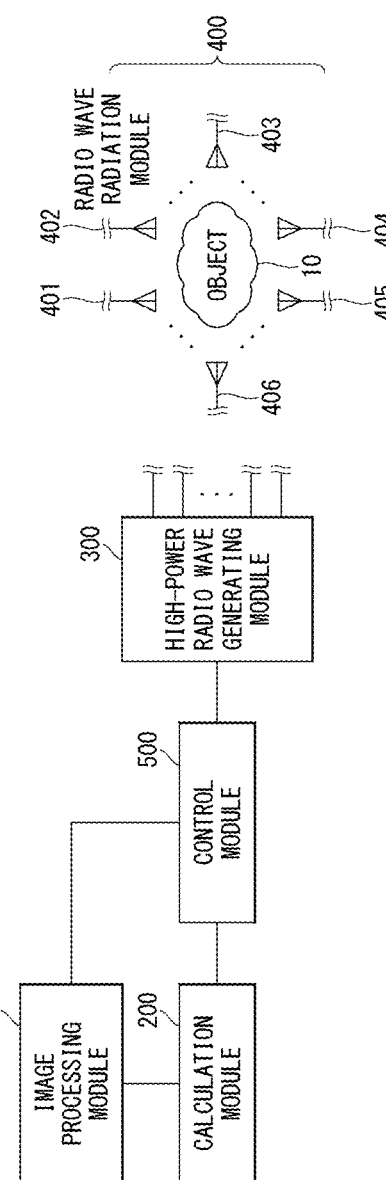
FIG. 1 is a block diagram of an apparatus for focusing radio wave energy according to one example embodiment of the present disclosure.

Embodiments of the present disclosure are disclosed herein. However, specific structural and functional details disclosed herein are merely representative for purposes of describing embodiments of the present disclosure. Thus, embodiments of the present disclosure may be embodied in many alternate forms and should not be construed as limited to embodiments of the present disclosure set forth herein.

Accordingly, while the present disclosure is capable of various modifications and alternative forms, specific embodiments thereof are shown by way of example in the drawings and will herein be described in detail. It should be understood, however, that there is no intent to limit the present disclosure to the particular forms disclosed, but on the contrary, the present disclosure is to cover all modifications, equivalents, and alternatives falling within the spirit and scope of the present disclosure. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

In exemplary embodiments of the present disclosure, "at least one of A and B" may refer to "at least one of A or B" or "at least one of combinations of one or more of A and B". In addition, "one or more of A and B" may refer to "one or more of A or B" or "one or more of combinations of one or more of A and B".

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between," "adjacent" versus "directly adjacent," etc.).

The terminology used herein is for the purpose of describing particular embodiments only and is not intended to be limiting of the present disclosure. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, preferred exemplary embodiments of the present disclosure will be described in more detail with reference to the accompanying drawings. In describing the present disclosure, in order to facilitate an overall understanding, the same reference numerals are used for the same elements in the drawings, and duplicate descriptions for the same elements are omitted.

FIG. 1 is a block diagram of an apparatus for focusing radio wave energy according to one example embodiment of the present disclosure.

Referring to FIG. 1, the apparatus for focusing radio wave energy, which removes an unnecessary focusing point 30, includes an image processing module 100, a calculation module 200, a high-power radio wave generating module 300, and a radio wave radiation module 400.

The image processing module 100 may receive an external image to generate an electromagnetic numerical model. Here, the image may be an internal tomography image of an object 10, such as a medical image captured using magnetic resonance imaging (MRI) or the like. The image processing module 100 may generate an electromagnetic numerical model enabling electromagnetic analysis of the object 10 in addition to electromagnetic characteristics of an internal medium thereof based on the received image.

The calculation module 200 may calculate a focusing parameter, in which radio waves are focused inside the object 10, based on the electromagnetic numerical model received from the image processing module 100. In addition to the electromagnetic numerical model received from the image processing module 100, the calculation module 200 may receive characteristic information of radiated radio waves.

The high-power radio wave generating module 300 may receive the focusing parameter calculated by the calculation module 200 to adjust the radio wave radiation module 400 to radiate radio waves. The radio wave radiation module 400 may include one or more radio wave radiation elements 401 to 406. In the radio wave radiation module 400, the radio wave radiation elements 401 to 406 may be disposed in a form which surrounds the object 10, but the present disclosure is not limited thereto.

The apparatus for focusing radio wave energy may further include a control module 500. The control module 500 may control the image processing module 100, the calculation module 200, the high-power radio wave generating module 300, and the radio wave radiation module 400.

Figure 2:
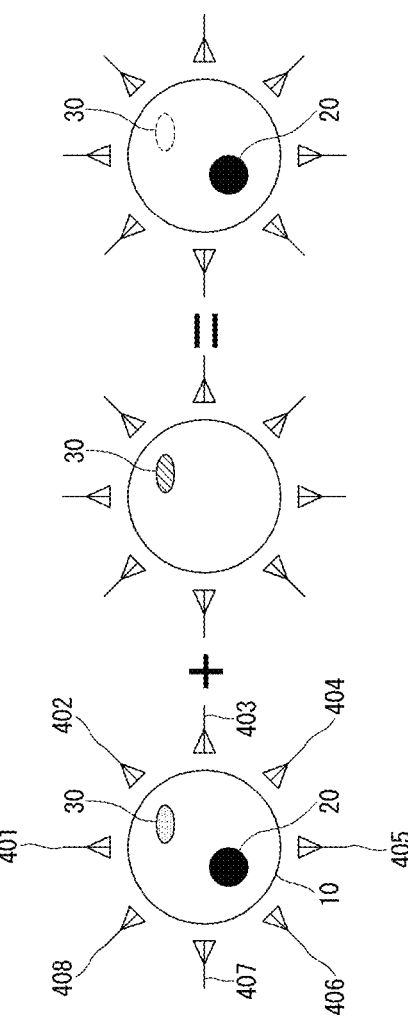
FIG. 2 shows conceptual diagrams of a method of removing an unnecessary focusing point according to one example embodiment of the present disclosure.

FIG. 2 shows conceptual diagrams of a method of removing an unnecessary focusing point according to one example embodiment of the present disclosure.

Referring to FIG. 2A, when an existing apparatus for focusing radio wave energy focuses radio waves at a focusing target point 20, an unnecessary focusing point 30, which is a point other than the focusing target point 20 at which radio wave energy is focused, may be generated.

Referring to FIGS. 2B and 2C, according to the present disclosure, the unnecessary focusing point 30 may be detected, and radio waves having an inverse phase may be generated at the detected unnecessary focusing point 30 to remove the generated unnecessary focusing point 30. In particular, as shown in FIG. 2B, the unnecessary focusing point 30 may be removed without affecting energy of the focusing target point 20.

In a method of removing the unnecessary focusing point 30, the unnecessary focusing point 30 may be removed by generating radio waves having a reverse phase at the generated unnecessary focusing point 30 other than the focusing target point 20. More specifically, in order to remove the unnecessary focusing point 30, a focusing parameter component $W_h$ for removing the unnecessary focusing point 30 may be combined with an existing focusing parameter $W_f$. Here, the component $W_h$ for removing the unnecessary focusing point 30 should not affect an electric field or power loss density (PLD) at a target point. To this end, data about a characteristic orthogonal to an electromagnetic characteristic value for focusing at the target point may be used. An electric field at a specific point may be expressed as the product of electromagnetic analysis result data of each irradiation device at a corresponding point and a focusing parameter. In addition, a PLD may be expressed as the product of the square of an electric field magnitude and conductivity. The electric field and the PLD may be mathematically represented by Equations 1 and 2.

$$E(r)=G(r)W_f \qquad \text{[Equation 1]}$$

$$PLD = \frac{1}{2}\sigma(r)E^2(r) \qquad \text{[Equation 2]}$$

Here, when the component $W_h$ for removing the unnecessary focusing point 30 is orthogonal to an electromagnetic characteristic value $G(r_0)$ at a target point $r_0$, a change amount of an electric field at the target point becomes "0," and thus there is no change in the electric field or PLD.

$$G(r_0){\perp}W_h{\rightarrow}G(r_0)(W_f{+}W_h){=}G(r_0)W_f \qquad \text{[Equation 3]}$$

In this case, based on orthogonal components obtained by performing a singular value decomposition on the electromagnetic characteristic value $G(r_0)$ at the target point, $W_h$ may be calculated by linearly combining orthogonal components to satisfy Equation 4 at the unnecessary focusing point 30 $r_p$ (=1, . . . , P). Here, the singular value decomposition may be a method of decomposing a matrix into a specific structure and may be a method of generalizing a spectral theory of a matrix to an arbitrary rectangular matrix. Through the singular value decomposition, it is possible to extract a component orthogonal to an electromagnetic characteristic value at a focusing target point.

$$G(r_p)(W_f{+}W_h){=}0 \qquad \text{[Equation 4]}$$

Electric fields inside the object 10 by $W_f$ and $W_h$ have opposite signs at the unnecessary focusing point 30, and as a result, when $W_f{+}W_h$ is used as a focusing parameter, an electric field at the unnecessary focusing point 30 may ultimately become "0." Although an electric field has been described here, the present disclosure is not limited thereto, and a PLD may be used instead of the electric field.

Figure 3:
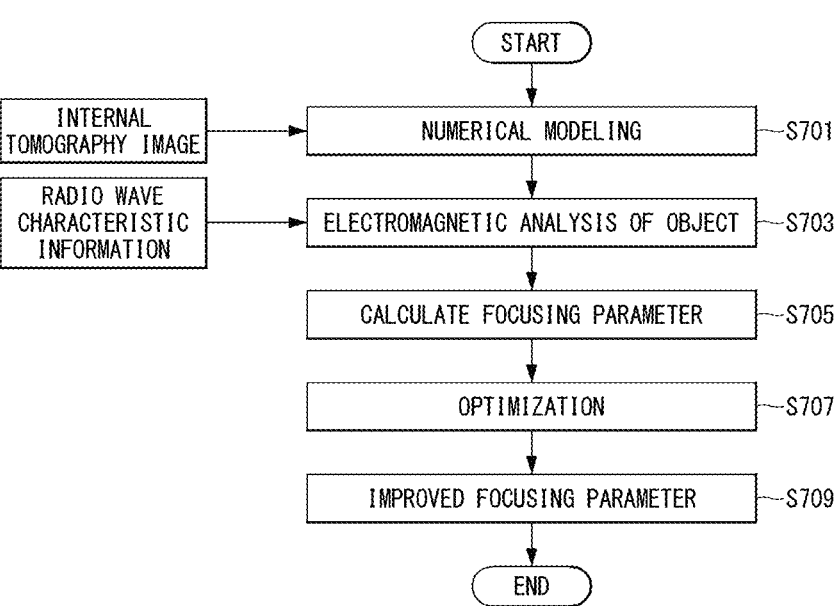
FIG. 3 is a flowchart of a method of removing the unnecessary focusing point 30 according to one example embodiment of the present disclosure.

FIG. 3 is a flowchart of a method of removing the unnecessary focusing point 30 according to one example embodiment of the present disclosure.

First, numerical modeling may be performed to enable electromagnetic analysis of the object 10 including the focusing target point 20 (S701). Here, the electromagnetic numerical model may be numerically modeled using an internal tomography image of the object 10, such as a medical image of a focusing object. In addition, for the electromagnetic numerical model, radio waves are radiated directly onto the focusing object in a preliminary operation to acquire information for generating an electromagnetic numerical model such as permittivity, conductivity, and impedance of the object 10.

Electromagnetic analysis of the object 10 may be performed through the generated electromagnetic numerical model using radio wave characteristic information (S703). Here, radio wave radiation characteristics of the radio wave radiation elements of the radio wave radiation module 400 may be used. Through the operation of the electromagnetic analysis, electromagnetic analysis of an object medium may be performed on the electromagnetic numerical model.

The calculation module 200 may calculate a focusing parameter based on the electromagnetic numerical model and the electromagnetic analysis of the object 10 (S705). The calculation module 200 may extract an initial focusing parameter and data about a characteristic orthogonal to an electromagnetic characteristic value for focusing radio wave energy at the focusing target point 20. The high-power radio wave generating module 300 radiates radio waves through the radio wave radiation module 400 using the initial focusing parameter. In this case, radio waves may be focused at the focusing target point 20, but the unnecessary focusing point 30 other than the focusing target point 20 at which radio waves are focused may be generated.

An improved focusing parameter in which the unnecessary focusing point 30 is not generated may be calculated through an optimization process S707 (S709). Here, the initial focusing parameter may be referred to as a first focusing parameter. A second focusing parameter may be an improved focusing parameter capable of removing the unnecessary focusing point 30 generated when the first focusing parameter is applied.

Figure 4:
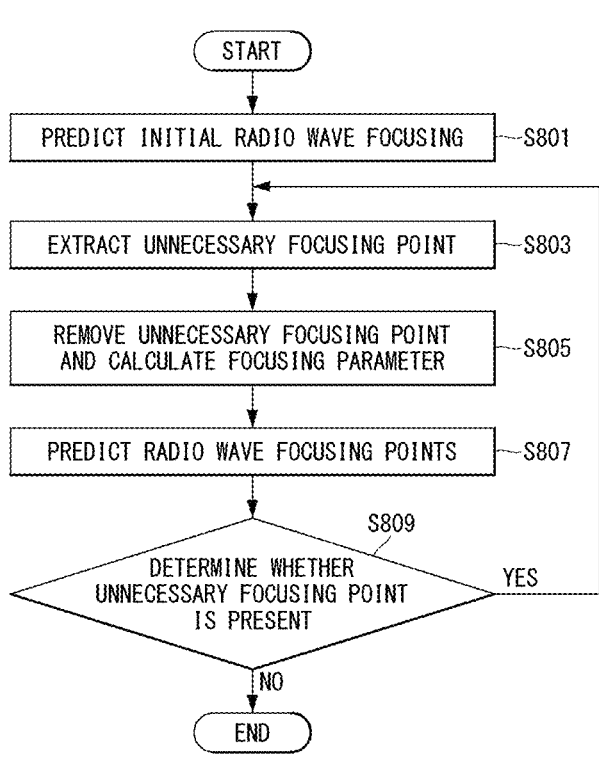
FIG. 4 is a flowchart of an optimization process of removing the unnecessary focusing point 30 according to one example embodiment of the present disclosure.

FIG. 4 is a flowchart of an optimization process of removing the unnecessary focusing point 30 according to one example embodiment of the present disclosure.

Radio wave focusing points of the first focusing parameter may be predicted based on the first focusing parameter using the electromagnetic numerical model of the object 10 and radio wave characteristic information (S801). The unnecessary focusing point 30 may be extracted from the predicted focusing points rather than the focusing target point 20 (S803). In this case, the unnecessary focusing point 30 may be a point other than the focusing target point 20 on which an amount of focused energy is greater than or equal to a certain threshold value. More specifically, the unnecessary focusing point 30 may be extracted using a PLD related to an amount of heat applied to the inside of the object 10 and may be extracted as a point at which the PLD is higher than or equal to a certain level as compared with the focusing target point 20 or a nearby point at which the PLD is the highest level. The unnecessary focusing point 30 may be derived as a point having an intermediate value among focusing points constituting a radio wave focusing distribution except for the focusing target point 20. In addition, the unnecessary focusing point 30 may be extracted as a point having a maximum value among the focusing points constituting the radio wave focusing distribution except for the focusing target point 20. Through the calculation process described with reference to FIG. 2, the second focusing parameter capable of removing the unnecessary focusing point 30 may be calculated (S805). Radio wave focusing points of the second focusing parameter may be predicted based on the second focusing parameter using the electromagnetic numerical model of the object 10 and radio wave characteristic information (S807). It may be determined whether the unnecessary focusing point 30 is present in the predicted radio focusing points of the second focusing parameter (S809). When the unnecessary focusing point 30 is present, operations S803 to S809 may be repeatedly performed based on the second focusing parameter. On the other hand, when the unnecessary focusing point 30 is not present, the second focusing parameter may be output and transferred to the high-power radio wave generating module 300.

FIGS. 5A to 5D show diagrams showing results of using an apparatus for removing the unnecessary focusing point 30 according to one example embodiment of the present disclosure.

Figure 5A:
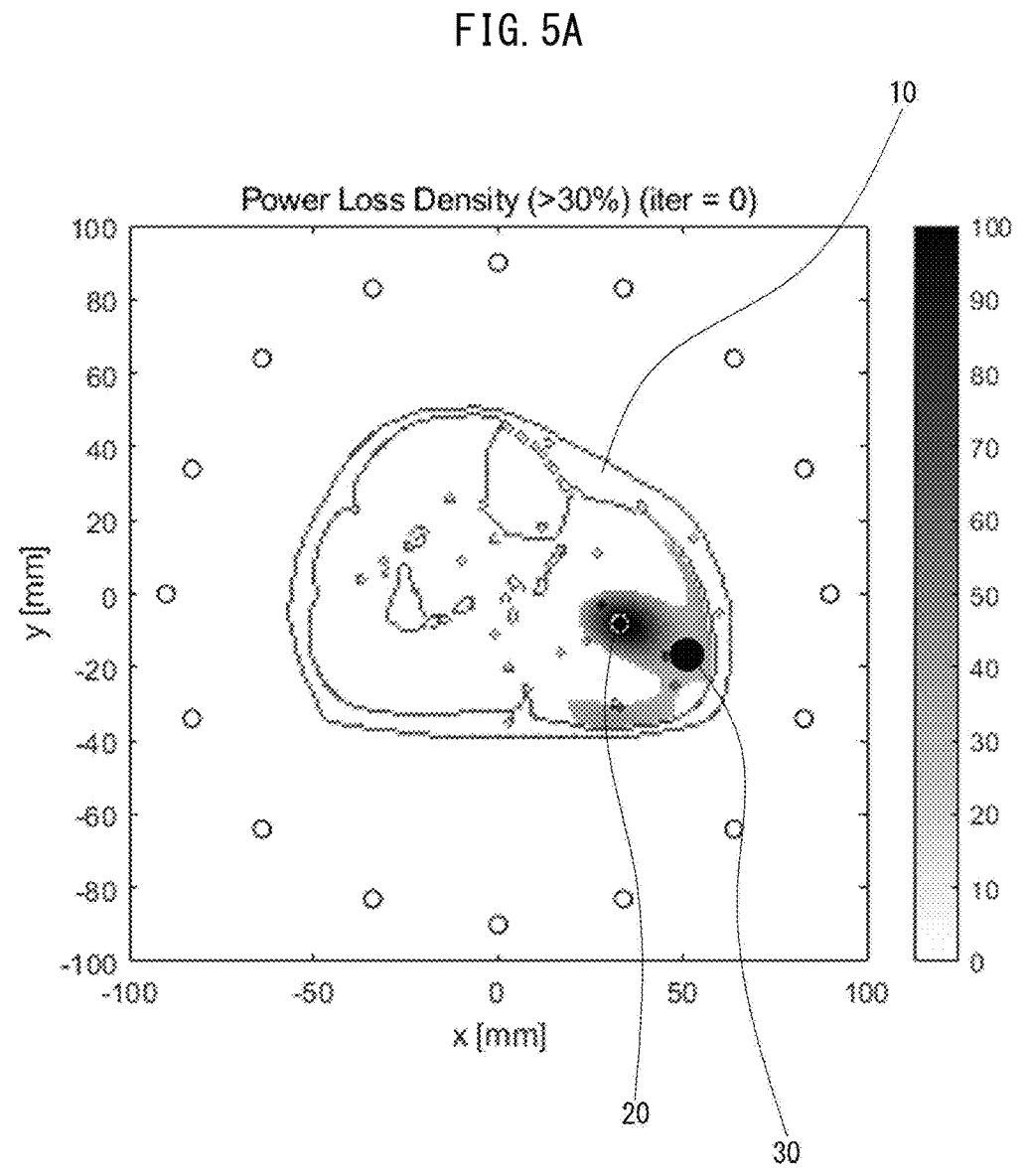
Figure 5B:
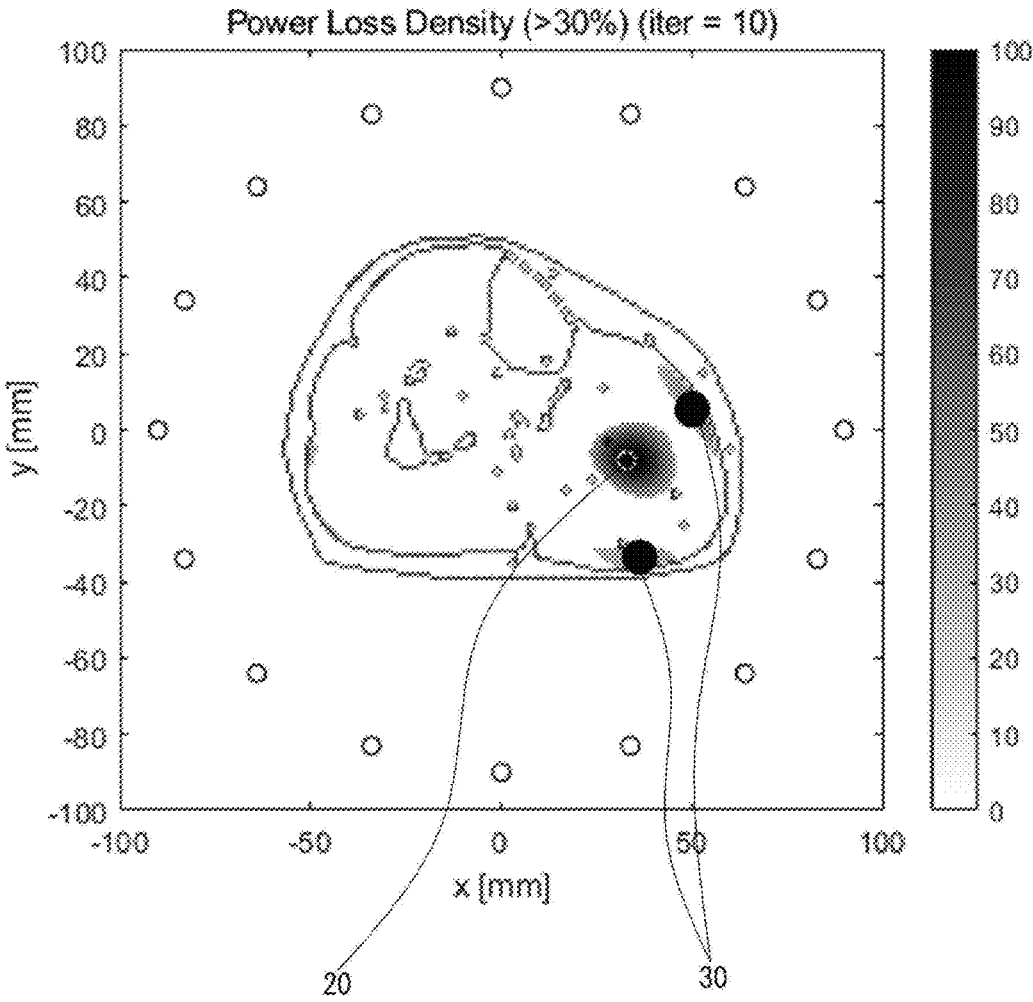
Figure 5C:
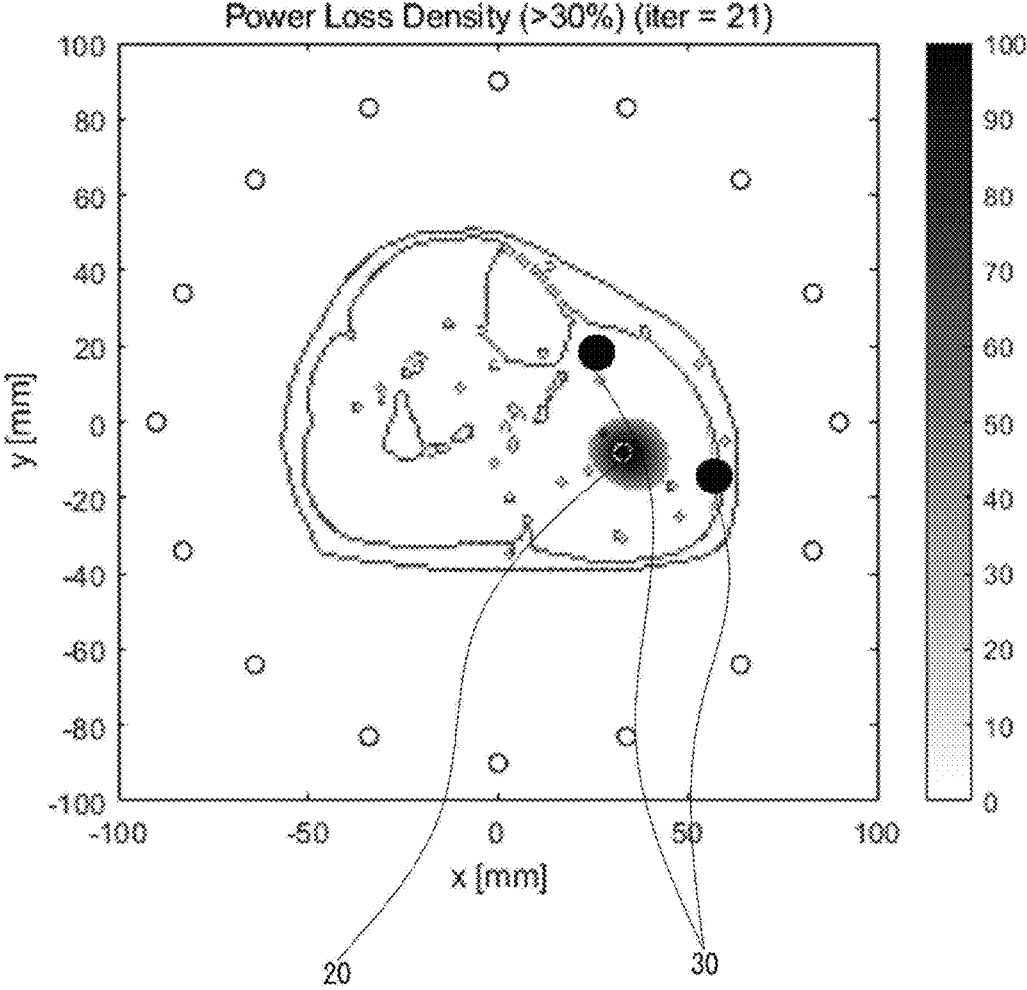
Figure 5D:
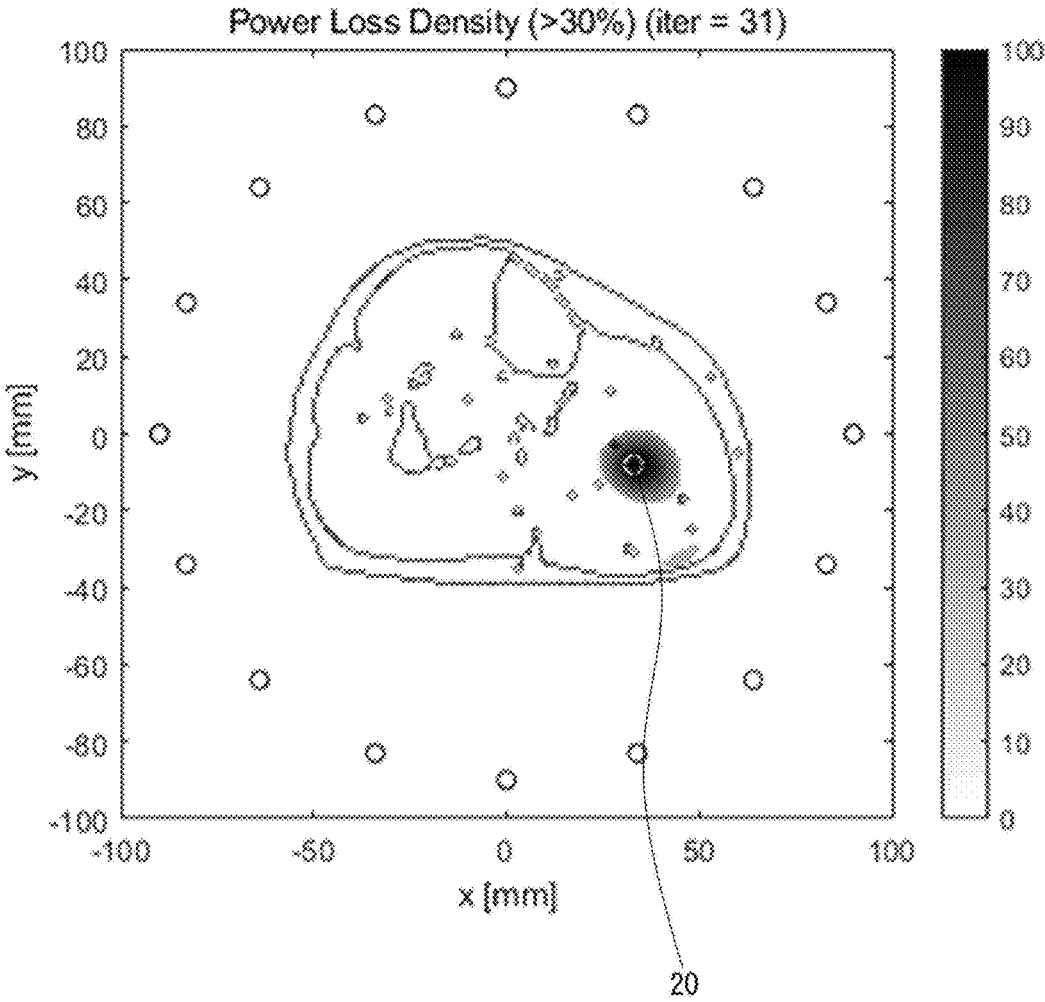

When radio waves are radiated onto the focusing target point 20 inside the object 10, the unnecessary focusing point 30 other than the focusing target point 20 may be generated as shown in FIG. 5A. When radio waves that are orthogonal to the focusing target point 20 and have a reverse phase at the unnecessary focusing point 30 are generated and radiated to remove the unnecessary focusing point 30, the unnecessary focusing point 30 of FIG. 5B can be removed. However, referring to FIG. 5B, another unnecessary focusing point 30 may be generated at a point other than the removed unnecessary focusing point 30 of FIG. 5A. Therefore, as shown in FIGS. 5B to 5C, a process of removing the generated unnecessary focusing point 30 may be repeatedly performed to remove the unnecessary focusing point 30 before only the focusing target point 20 is finally present as shown in FIG. 5D.

According to the present disclosure, radio wave energy is focused only at the focusing target point 20, thereby solving a problem in which radio wave energy is transmitted to an undesired position other than a target point, and energy is concentrated in and damages a normal area during non-invasive treatment. In addition, in an existing method, in order to solve a problem in which radio wave energy is focused at an unintended position, a temperature monitoring device and a cooling device for cooling are additionally provided, or a medical professional monitors a system at all times during treatment and stops the system when the problem occurs and performs work of re-operating the system after a certain period of time. However, in the present disclosure, there is an effect of not requiring additional equipment or standby manpower by preventing radio waves from being focused anywhere other than a target point.

The operations of the method according to the exemplary embodiment of the present disclosure can be implemented as a computer readable program or code in a computer readable recording medium. The computer readable recording medium may include all kinds of recording apparatus for storing data which can be read by a computer system. Furthermore, the computer readable recording medium may store and execute programs or codes which can be distributed in computer systems connected through a network and read through computers in a distributed manner.

The computer readable recording medium may include a hardware apparatus which is specifically configured to store and execute a program command, such as a ROM, RAM or flash memory. The program command may include not only machine language codes created by a compiler, but also high-level language codes which can be executed by a computer using an interpreter.

Although some aspects of the present disclosure have been described in the context of the apparatus, the aspects may indicate the corresponding descriptions according to the method, and the blocks or apparatus may correspond to the steps of the method or the features of the steps. Similarly, the aspects described in the context of the method may be expressed as the features of the corresponding blocks or items or the corresponding apparatus. Some or all of the steps of the method may be executed by (or using) a hardware apparatus such as a microprocessor, a programmable computer or an electronic circuit. In some embodiments, one or more of the most important steps of the method may be executed by such an apparatus.

In some exemplary embodiments, a programmable logic device such as a field-programmable gate array may be used to perform some or all of functions of the methods described herein. In some exemplary embodiments, the field-programmable gate array may be operated with a microprocessor to perform one of the methods described herein. In general, the methods are preferably performed by a certain hardware device.

The description of the disclosure is merely exemplary in nature and, thus, variations that do not depart from the substance of the disclosure are intended to be within the scope of the disclosure. Such variations are not to be regarded as a departure from the spirit and scope of the disclosure. Thus, it will be understood by those of ordinary skill in the art that various changes in form and details may be made without departing from the spirit and scope as defined by the following claims.

What is claimed is:

1. A method of focusing radio wave energy at a focusing target point, which is performed by a processor, the method comprising:

generating an electromagnetic numerical model of an object including the focusing target point;

predicting radio wave focusing points inside the object using radio wave characteristic information of a radio wave radiation module and the electromagnetic numerical model;

optimizing one or more focusing parameters such that radio wave energy reaching one or more unnecessary focusing points other than the focusing target point among the radio wave focusing points inside the object is reduced; and radiating radio waves based on the optimized focusing parameters.

2. The method of claim 1, wherein the electromagnetic numerical model is generated using an internal tomography image of the object.

3. The method of claim 1, wherein:

the generating of the electromagnetic numerical model further includes a preliminary measurement operation of acquiring information about permittivity, conductivity, and/or impedance of the object using the radio waves to be radiated; and the electromagnetic numerical model is generated based on a result of the preliminary measurement operation.

4. The method of claim 1, wherein a magnitude and a phase of the radio waves are adjusted using the optimized focusing parameters.

5. The method of claim 1, wherein the optimizing of the focusing parameters includes:

operation (a) of extracting the unnecessary focusing points inside the object based on a first focusing parameter;

operation (b) of calculating a second focusing parameter for reducing the radio wave energy focused on the extracted unnecessary focusing points;

operation (c) of predicting the radio wave focusing points inside the object based on the second focusing parameter; and an operation of repeatedly performing operations (a) to (c) before the unnecessary focusing points are not extracted.

6. The method of claim 5, wherein the unnecessary focusing points are points having an intermediate value among points in the object at which the radio wave energy is focused to exceed a certain threshold value.

7. The method of claim 5, wherein the calculating of the second focusing parameter further includes:

calculating a parameter having a reverse phase of the radio wave energy focused at the unnecessary focusing points; and combining the first focusing parameter and the parameter having the reverse phase.

8. The method of claim 7, wherein the parameter having the reverse phase at the unnecessary focusing points is orthogonal to an electromagnetic characteristic value at the focusing target point.

9. An apparatus for focusing radio wave energy, the apparatus comprising:

a memory in which one or more instructions are stored; and a processor configured to execute the one or more instructions stored in the memory, wherein the processor configured to execute the one or more instructions performs:

an operation of generating an electromagnetic numerical model of an object including a focusing target point;

an operation of predicting radio wave focusing points inside the object using radio wave characteristic information of a radio wave radiation module and the electromagnetic numerical model;

an operation of optimizing one or more focusing parameters such that radio wave energy reaching one or more unnecessary focusing points other than the focusing target point among the radio wave focusing points inside the object is reduced; and an operation of radiating radio waves based on the optimized focusing parameters.

10. The apparatus of claim 9, wherein the electromagnetic numerical model is generated using an internal tomography image of the object.

11. The apparatus of claim 9, wherein:

the operation of, by the processor, generating the electromagnetic numerical model further includes a preliminary measurement operation of acquiring information about permittivity, conductivity, and/or impedance of the object using the radio waves to be radiated; and the electromagnetic numerical model is generated based on a result of the preliminary measurement operation.

12. The apparatus of claim 9, wherein a magnitude and a phase of the radio waves are adjusted using the optimized focusing parameters.

13. The apparatus of claim 9, wherein the operation of, by the processor, optimizing the focusing parameters includes:

operation (a) of extracting the unnecessary focusing points inside the object based on a first focusing parameter;

operation (b) of calculating a second focusing parameter for reducing the radio wave energy focused on the extracted unnecessary focusing points;

operation (c) of predicting the radio wave focusing points inside the object based on the second focusing parameter; and an operation of repeatedly performing operations (a) to (c) before the unnecessary focusing points are not extracted.

14. The apparatus of claim 13, wherein the unnecessary focusing points are points having an intermediate value among points in the object at which the radio wave energy is focused to exceed a certain threshold value.

15. The apparatus of claim 13, wherein the operation of, by the processor, calculating the second focusing parameter further includes:

calculating a parameter having a reverse phase of the radio wave energy focused at the unnecessary focusing points; and combining the first focusing parameter and the parameter having the reverse phase.

16. The apparatus of claim 15, wherein the parameter having the reverse phase at the unnecessary focusing points is orthogonal to an electromagnetic characteristic value at the focusing target point.

17. A method of optimizing one or more focusing parameters, which is executed by a processor, the method comprising:

operation (a) of extracting one or more unnecessary focusing points inside an object including a focusing target point based on a first focusing parameter;

operation (b) of calculating a second focusing parameter for reducing radio wave energy focused on the extracted unnecessary focusing points;

operation (c) of predicting one or more radio wave focusing points inside the object based on the second focusing parameter;

an operation of repeatedly performing operations (a) to (c) before the unnecessary focusing points are not extracted; and an operation of outputting the second focusing parameter in which the unnecessary focusing points are not extracted.

18. The method of claim 17, wherein the unnecessary focusing points are points having an intermediate value among points in the object at which the radio wave energy is focused to exceed a certain threshold value.

19. The method of claim 17, wherein the operation of, by the processor, calculating the second focusing parameter further includes:

calculating a parameter having a reverse phase of the radio wave energy focused at the unnecessary focusing points; and combining the first focusing parameter and the parameter having the reverse phase.

20. The method of claim 19, wherein the parameter having the reverse phase at the unnecessary focusing points is orthogonal to an electromagnetic characteristic value at the focusing target point.

* * * * *